United States Patent
Wales et al.

(10) Patent No.: US 6,964,363 B2
(45) Date of Patent: Nov. 15, 2005

(54) SURGICAL STAPLING INSTRUMENT HAVING ARTICULATION JOINT SUPPORT PLATES FOR SUPPORTING A FIRING BAR

(75) Inventors: Kenneth S. Wales, Mason, OH (US); Joseph Charles Heuil, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/615,971

(22) Filed: Jul. 9, 2003

(65) Prior Publication Data

US 2005/0006429 A1 Jan. 13, 2005

(51) Int. Cl.⁷ .............................................. A61B 17/068
(52) U.S. Cl. ................... 227/175.1; 227/180.1; 227/19
(58) Field of Search ................ 227/19, 176.1, 227/180.1, 175.1

(56) References Cited

U.S. PATENT DOCUMENTS

| | | | | |
|---|---|---|---|---|
| 5,312,023 A | * | 5/1994 | Green et al. ............. | 227/175.1 |
| 5,456,684 A | | 10/1995 | Schmidt et al. | |
| 5,562,682 A | | 10/1996 | Oberlin et al. | |
| 5,673,840 A | | 10/1997 | Schulze et al. | |
| 5,743,456 A | * | 4/1998 | Jones et al. ............. | 227/176.1 |
| 5,797,537 A | | 8/1998 | Oberlin et al. | |
| 5,820,007 A | * | 10/1998 | Crowley .................... | 226/31 |
| 5,855,311 A | * | 1/1999 | Hamblin et al. ......... | 227/176.1 |
| 6,010,054 A | * | 1/2000 | Johnson et al. ........... | 227/176.1 |
| 6,241,139 B1 | * | 6/2001 | Milliman et al. ......... | 227/175.1 |
| 6,330,965 B1 | * | 12/2001 | Milliman et al. ......... | 227/176.1 |
| 6,644,532 B2 | * | 11/2003 | Green et al. ............. | 227/176.1 |
| 6,681,978 B2 | * | 1/2004 | Geiste et al. ............ | 227/176.1 |
| 2001/0021859 A1 | | 9/2001 | Toshikazu et al. | |
| 2004/0050902 A1 | | 3/2004 | Green et al. | |

FOREIGN PATENT DOCUMENTS

WO     WO 01/00095     1/2001

* cited by examiner

*Primary Examiner*—Rinaldi I. Rada
*Assistant Examiner*—Paul Durand

(57) ABSTRACT

A surgical stapling and severing instrument particularly suited to endoscopic articulates an end effector by having a geared articulation mechanism that converts rotational motion from a handle portion. A firing bar longitudinally translates between the handle portion and the end effector. The firing bar head is thickened in order to present an undistorted cutting edge and engagement features to the opposing jaws of the end effector. The firing bar also advantageously includes a thinned or tapered proximal portion in the form of a strip or band that negotiates the articulation mechanism flexibility. To prevent buckling of the firing bar strip during firing, a pair of support plates adjustably flank the firing bar strip through the articulation mechanism. Various versions show resilient and spring engagement of each end of the support plate to distal and proximal sides of the articulation mechanism, as well as a resilient support plate.

7 Claims, 18 Drawing Sheets

SURGICAL STAPLING INSTRUMENT HAVING ARTICULATION JOINT SUPPORT PLATES FOR SUPPORTING A FIRING BAR

CROSS REFERENCE TO RELATED APPLICATIONS

The present application is related to four co-pending and commonly-owned applications filed on even date herewith, the disclosure of each is hereby incorporated by reference in their entirety, these four applications being respectively entitled:

(1) "SURGICAL STAPLING INSTRUMENT INCORPORATING A TAPERED FIRING BAR FOR INCREASED FLEXIBILITY AROUND THE ARTICULATION JOINT" to Frederick E. Shelton IV, Mike Setser, and Bruce Weisenburgh;

(2) "SURGICAL STAPLING INSTRUMENT INCORPORATING AN ARTICULATION JOINT FOR A FIRING BAR TRACK" to Douglas B. Hoffman;

(3) "SURGICAL INSTRUMENT INCORPORATING AN ARTICULATION MECHANISM HAVING ROTATION ABOUT THE LONGITUDINAL AXIS" to Kenneth S. Wales, Douglas B. Hoffman, Frederick E. Shelton IV, and Jeff Swayze; and (4) "A SURGICAL INSTRUMENT WITH A LATERAL-MOVING ARTICULATION CONTROL" to Kenneth S. Wales.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments that include an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally these endoscopic surgical instruments include a long shaft between the end effector and a handle portion manipulated by the clinician, this long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

Depending upon the nature of the operation, it may be desirable to further adjust the positioning of the end effector of an endoscopic surgical instrument rather than being limited to insertion and rotation. In particular, it is often desirable to orient the end effector at an axis transverse to the longitudinal axis of the shaft of the instrument. The transverse movement of the end effector relative to the instrument shaft is conventionally referred to as "articulation". This articulated positioning permits the clinician to more easily engage tissue in some instances. In addition, articulated positioning advantageously allows an endoscope to be positioned behind the end effector without being blocked by the instrument shaft.

While the aforementioned non-articulating stapling and severing instruments have great utility and may be successfully employed in many surgical procedures, it is desirable to enhance their operation with the ability to articulate the end effector, thereby giving greater clinical flexibility in their use. Articulating surgical instruments generally use one or more firing bars that move longitudinally within the instrument shaft and through the articulation joint to fire the staples from the cartridge and to cut the tissue between the innermost staple lines. One common problem with these surgical instruments is control of the firing bar through the articulation joint. At the articulation joint, the end effector is longitudinally spaced away from the shaft so that the edges of the shaft and end effector don't collide during articulation. This gap must be filled with support material or structure to prevent the firing bar from buckling out of the joint when the single or multiple firing bars is subjected to longitudinal firing loads. What is needed is a support structure that guides and supports the single or multiple firing bars through the articulation joint and bends or curves as the end effector is articulated.

U.S. Pat. No. 5,673,840 describes a flexible articulation joint that is formed from an elastomeric or plastic material that bends at the flexible joint or "flex neck". The firing bars are supported and guided through a hollow tube within the flex neck. The flex neck is a portion of the jaw closure mechanism and moves longitudinally relative to the end effector, shaft, and firing bars when the jaws are closed on tissue. The firing bars then move longitudinally within the flex neck as the staples are fired and tissue is cut.

U.S. Pat. No. 5,797,537 to Allen describes an articulation joint that pivots around a pin, rather than bends around a flex joint. In this instrument, firing bars are supported between a pair of spaced support plates connected at one end to the shaft and at another end to the end effector. At least one of those connections is a slidable connection. The support plates extend through the articulation joint adjacent to the flexible drive member in the plane of articulation such that the support plates bend through the gap in the plane of articulation and the flexible firing bar bends against the support when the tip is articulated in one direction from its aligned position. U.S. Pat. No. 6,330,965 from U.S. Surgical teaches the use of support plates that are fixedly attached to the shaft and slidably attached to the end effector.

Although these known support plates guide a firing bar through an articulation joint, it is believed that performance may be enhanced. For instance, it is often desirable for the firing bar to be rapidly accelerated during firing in order to ensure sufficient momentum to sever tissue effectively. Rigidly attached support plates may tend to dislodge in response, allowing the firing bar to blow out from the articulation joint. As a further example, it is desirable for the instrument to operate in the same manner whether articulated or not. Increased friction when articulated would be inconvenient and distracting to the clinician if required to exert a varying amount of firing force.

Consequently, a significant need exists for an improved articulation mechanism for a surgical instrument mechanisms that provides enhanced support to a firing bar through the articulation joint.

BRIEF SUMMARY OF THE INVENTION

The invention overcomes the above-noted and other deficiencies of the prior art by providing an articulating surgical instrument that actuates an end effector with a longitudinally translating firing mechanism advantageously supported through an articulation mechanism by flanking support plates. In order to better respond to firing loads on the firing mechanism, one or more ends of each support plate are resiliently or springedly engaged to one side of the articulation mechanism, and thus are better able to avoid buckling of the firing mechanism.

In one aspect of the invention, a surgical instrument has a handle portion that produces an articulation motion and a firing motion, both of which are transferred through a shaft to an articulation mechanism. The articulation mechanism responds to the articulation motion to rotate an end effector from the longitudinal axis of the shaft. A firing mechanism responds to the firing motion and is coupled for movement through the articulation mechanism and the end effector. A pair of support plates flank the firing mechanism across the articulation mechanism, each support plate including an end springedly engaged to a frame recess formed in the articulation mechanism to assist in preventing buckling of the firing mechanism out of the articulation mechanism. Thus various types of actuated diagnostic or therapeutic end effectors may be incorporated into an articulating surgical instrument without buckling at the articulation mechanism, even with high firing forces and reduces component dimensions for endoscopic use.

In another aspect of the invention, a surgical instrument has a handle portion that produces a firing motion, a closing motion, and an articulation motion, each transferred through a shaft. An articulation mechanism distally coupled to the shaft pivots an end effector in response to the articulation motion. The end effector includes an elongate channel coupled to the shaft, an anvil that is pivotally coupled to the elongate channel and that is responsive to the closing motion from the shaft. A firing device has a distally presented cutting edge longitudinally received between the elongate channel and the anvil. An articulation mechanism pivots the elongate channel from the shaft in response to the articulation motion. A pair of support plates flank the firing mechanism across the articulation mechanism, each support plate including an end springedly engaged to a frame recess formed in the articulation mechanism. Thereby, an improved stapling and severing instrument may incorporate a firing device that withstands high firing loads yet does not introduce significantly increased firing forces when articulated.

These and other objects and advantages of the present invention shall be made apparent from the accompanying drawings and the description thereof.

BRIEF DESCRIPTION OF THE FIGURES.

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
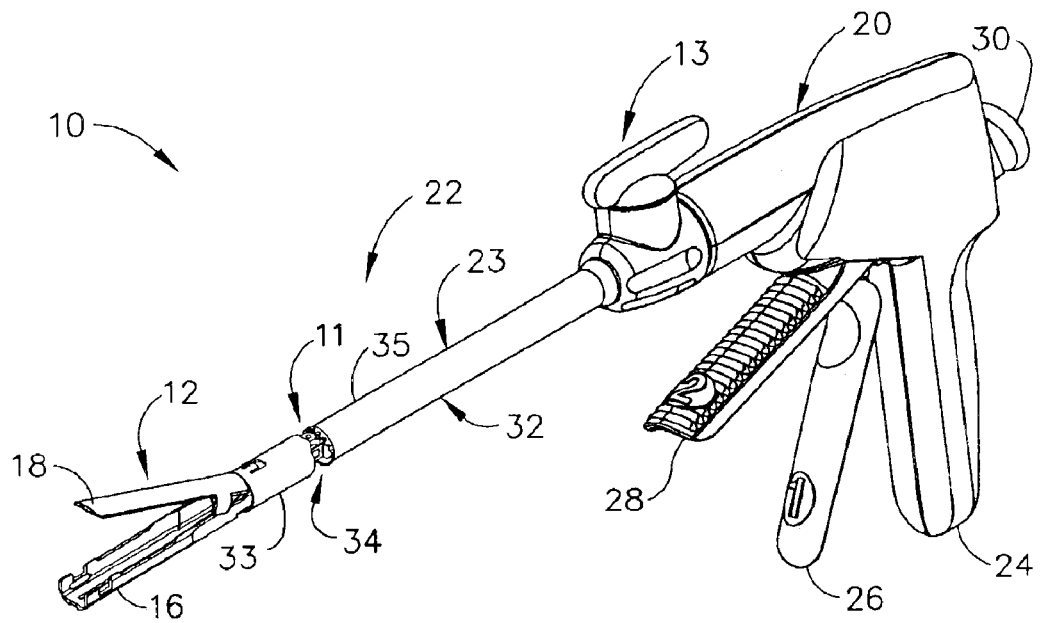
FIG. 1 is a perspective view of an articulating surgical instrument in a nonarticulated position.
Figure 2:
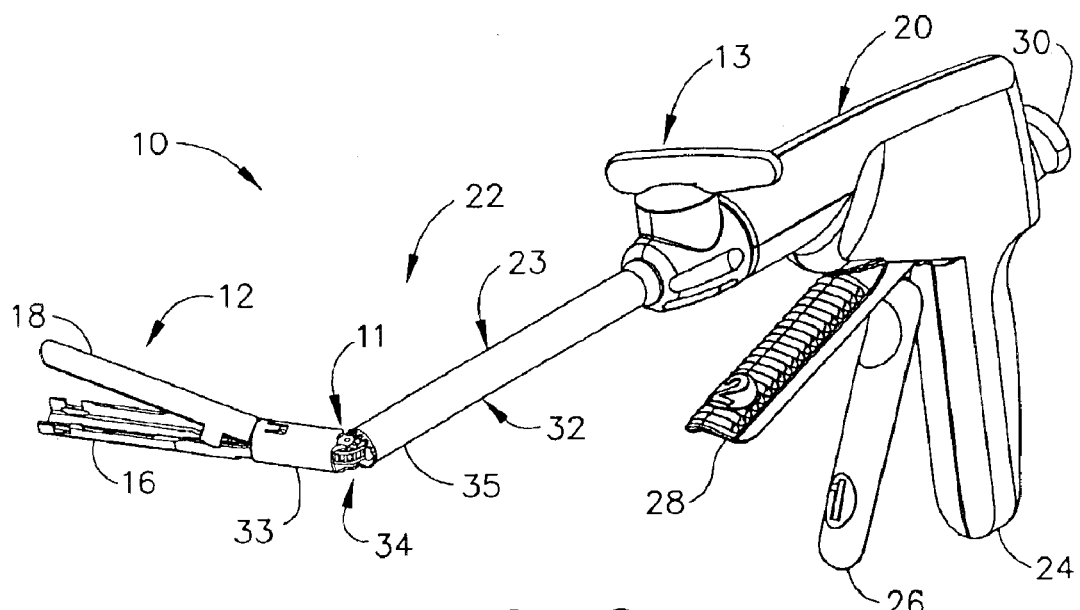
FIG. 2 is a perspective view of an articulating surgical instrument in an articulated position.
Figure 3:
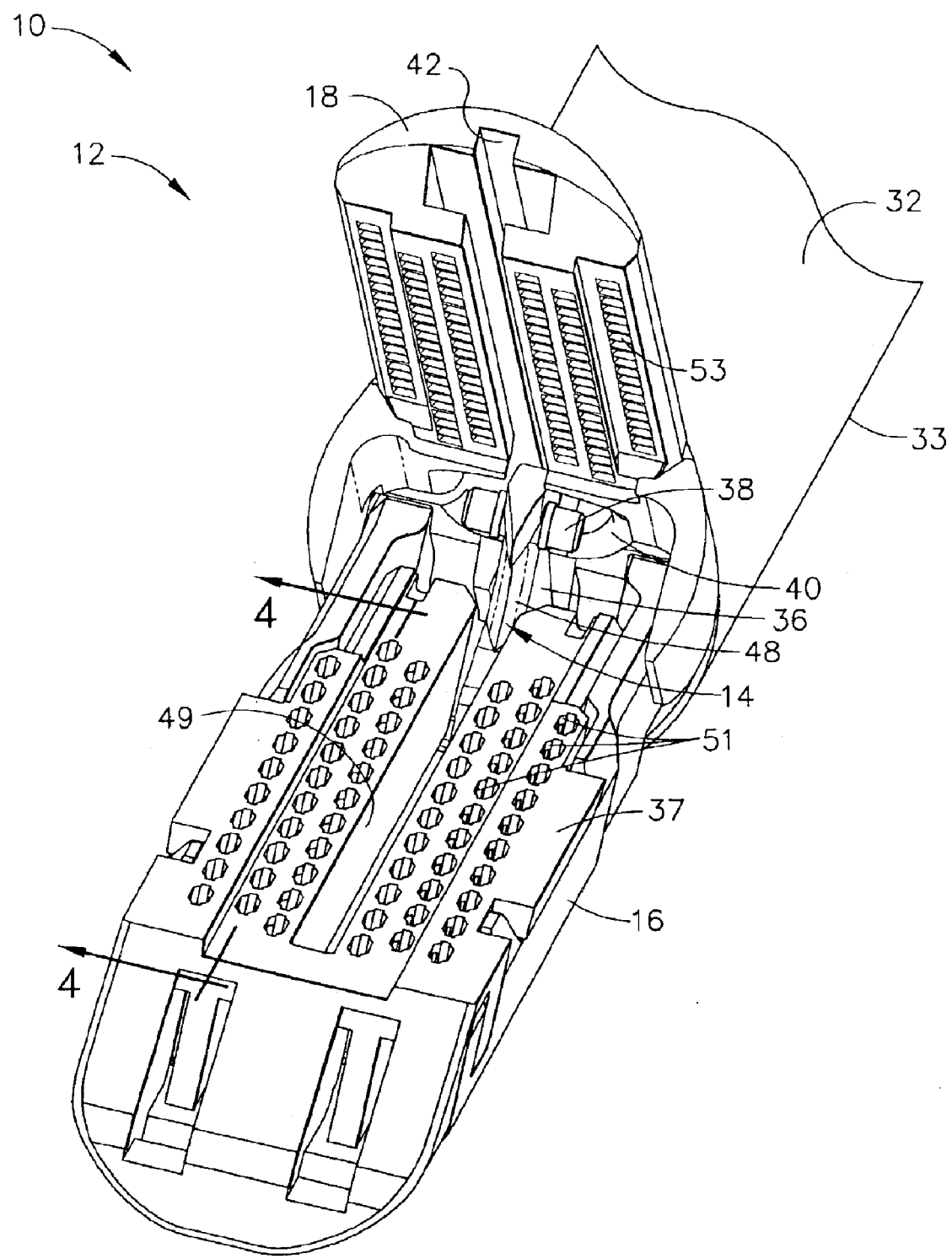
FIG. 3 is a perspective view of an opened end effector of the articulating surgical instrument of FIGS. 1–2.

Turning to the Drawings, wherein like numerals denote like components throughout the several views, FIGS. 1–3 depict a surgical instrument, which in the illustrative embodiment is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to a surgical site in a patient for performing a surgical procedure. Once an articulation mechanism 11 and a distally attached end effector 12 are inserted through the cannula passageway, the articulation mechanism 11 may be remotely articulated, as depicted in FIG. 2, by an articulation control 13. Thereby, the end effector 12 may reach behind an organ or approach tissue from a desired angle or for other reasons. For instance, a firing mechanism, advantageously depicted as an E-beam firing bar 14 (depicted in FIG. 3), that severs clamped tissue, engages an elongate channel 16 and a pivotally attached anvil 18.

The surgical and stapling and severing instrument 10 includes a handle portion 20 connected to an implement portion 22, the latter further comprising a shaft 23 distally terminating in the articulating mechanism 11 and the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12. Thereafter, a release button 30 is depressed to release the clamped tissue.

An outermost closure sleeve 32 of the shaft 23 longitudinally translates in response to the closure trigger 26 to pivotally close the anvil 18. Specifically, a distal portion, or closure ring 33, of the closure sleeve 32 with respect to the articulation mechanism 11 is indirectly supported by a frame 34 of the implement portion 22 (partially visible at the articulation mechanism 11). At the articulation mechanism 11, a proximal portion, or closure tube 35, of the closure sleeve 32 communicates with the distal portion (closure ring) 33. The frame 34 is flexibly attached to the elongate channel 16 via the articulation mechanism 11, enabling articulation in a single plane. The frame 34 also longitudinally slidingly supports a firing drive member 36 that communicates a firing motion from the firing trigger 28 to the firing bar 14. Only the firing bar 14 of the firing drive member 36 is depicted FIG. 3, but the firing drive member 36 is described below further detail with regard to various versions of a rotationally controlled articulation mechanism 11.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

E-Beam Firing Bar

Figure 4:
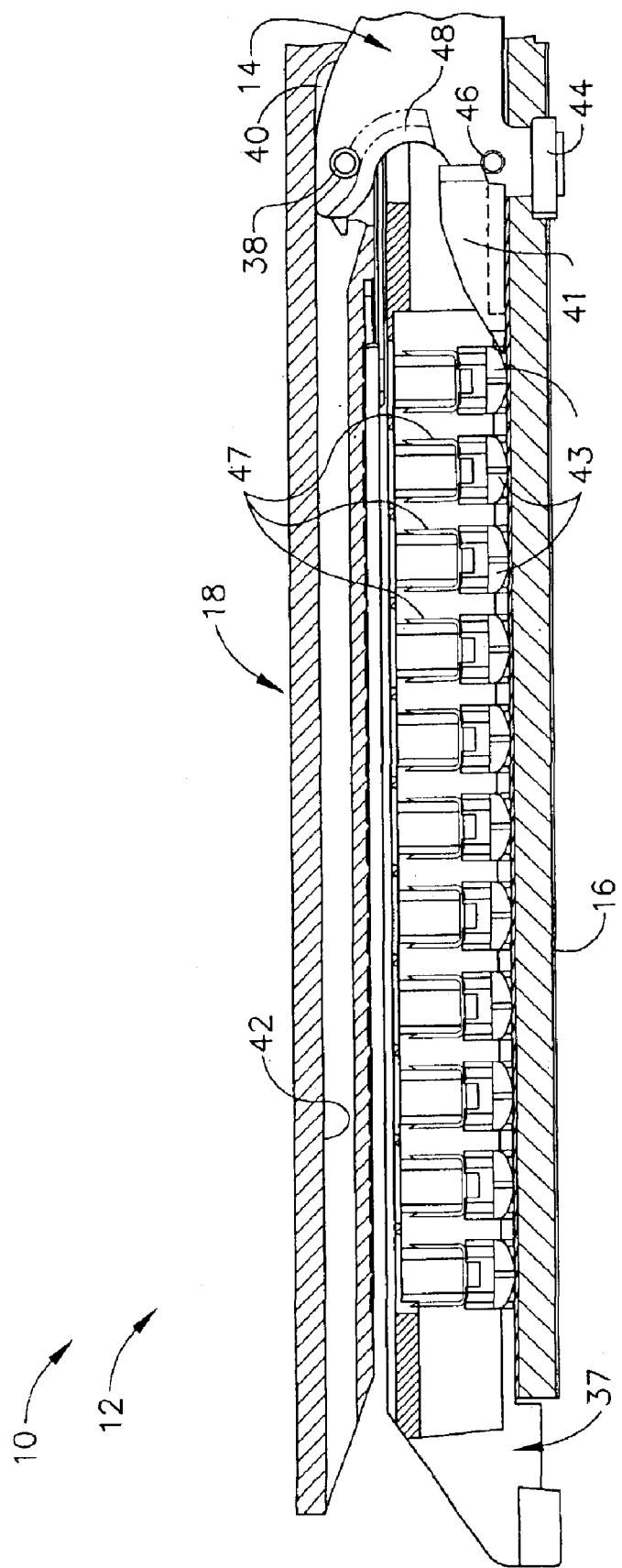
FIG. 4 depicts a side elevation view in section of the end effector of FIG. 3 of the surgical instrument of FIG. 1, the section generally taken along lines 4—4 of FIG. 3 to expose portions of a staple cartridge but also depicting the firing bar along the longitudinal centerline.
Figure 5:
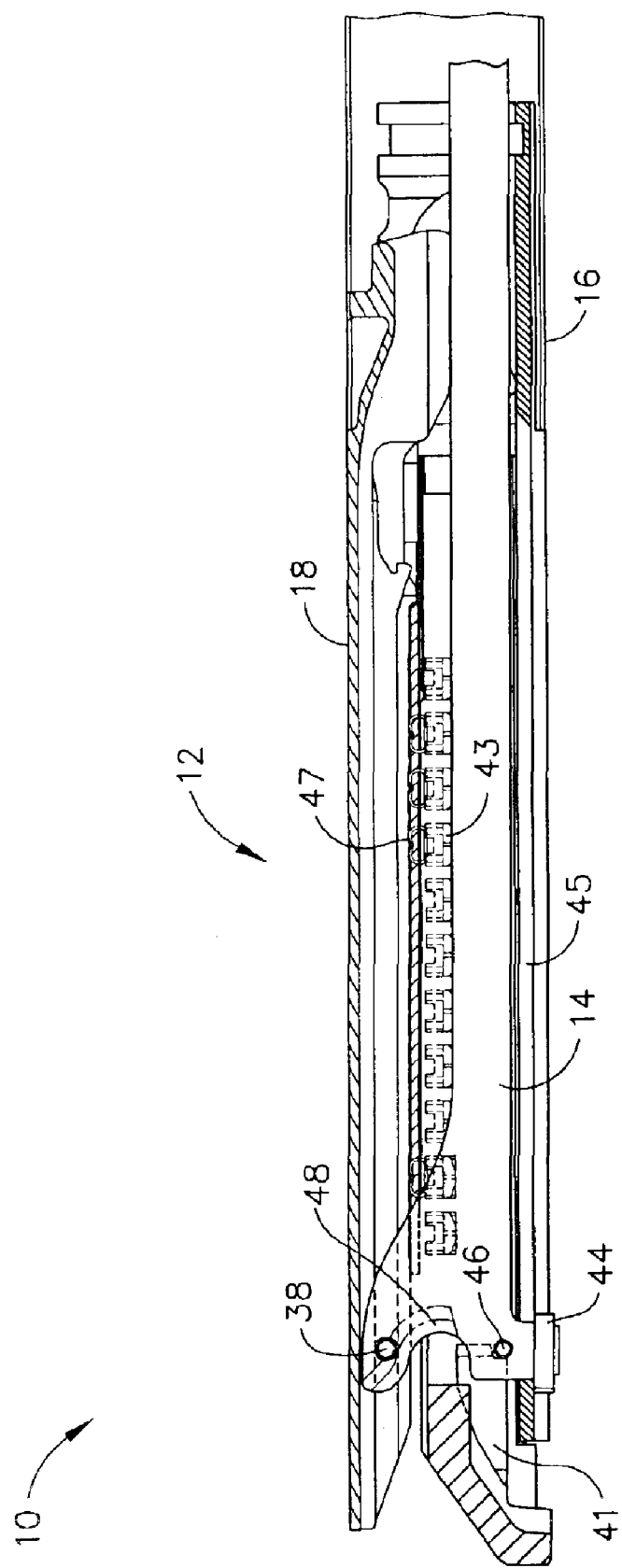
FIG. 5 depicts a side elevation view in section of the end effector of FIG. 4 after the firing bar has fully fired.

FIGS. 3–5 depict the end effector 12 employing the E-beam firing bar 14 to perform a number of functions. In FIG. 3, the firing bar 14 is proximally positioned, allowing an unspent staple cartridge 37 to be installed into the elongate channel 16. In particular, an upper pin 38 of the firing bar 14 resides within a recess, depicted as an anvil pocket 40 allowing the anvil 18 to be repeatedly opened and closed. With the end effector closed as depicted in FIG. 4, the firing bar 14 is advanced in engagement with the anvil 18 by having the upper pin 38 enter a longitudinal anvil slot 42. A lower most pin, or firing bar cap 44, engaged a lower surface of the elongate channel 16 by having the firing bar 14 extend through a channel slot 45. A middle pin 46 slidingly engages a top surface of the elongate channel 16, cooperating with the firing bar cap 44. Thereby, the firing bar 14 affirmatively spaces the end effector 12 during firing, overcoming pinching that may occur with a minimal amount of clamped tissue and overcoming staple malformation with an excessive amount of clamped tissue.

During firing, a distally presented cutting edge 48 between the upper pin 38 and middle pin 46 of the firing bar enters a proximally presented vertical slot 49 of the staple cartridge 37, severing tissue clamped between the staple cartridge 37 and the anvil 18. As shown in FIG. 4, the middle pin 46 actuates the staple cartridge 37 by entering into a firing slot within the staple cartridge 37, driving a wedge sled 41 into upward camming contact with staple drivers 43 that in turn drive a plurality of staples 47 out of staple apertures 51 in the staple cartridge 37 into forming contact with staple pockets 53 on an inner surface of the anvil 18. FIG. 5 depicts the firing bar 14 fully distally translated after completing severing and stapling tissue.

Two-Axis Handle

Figure 6:
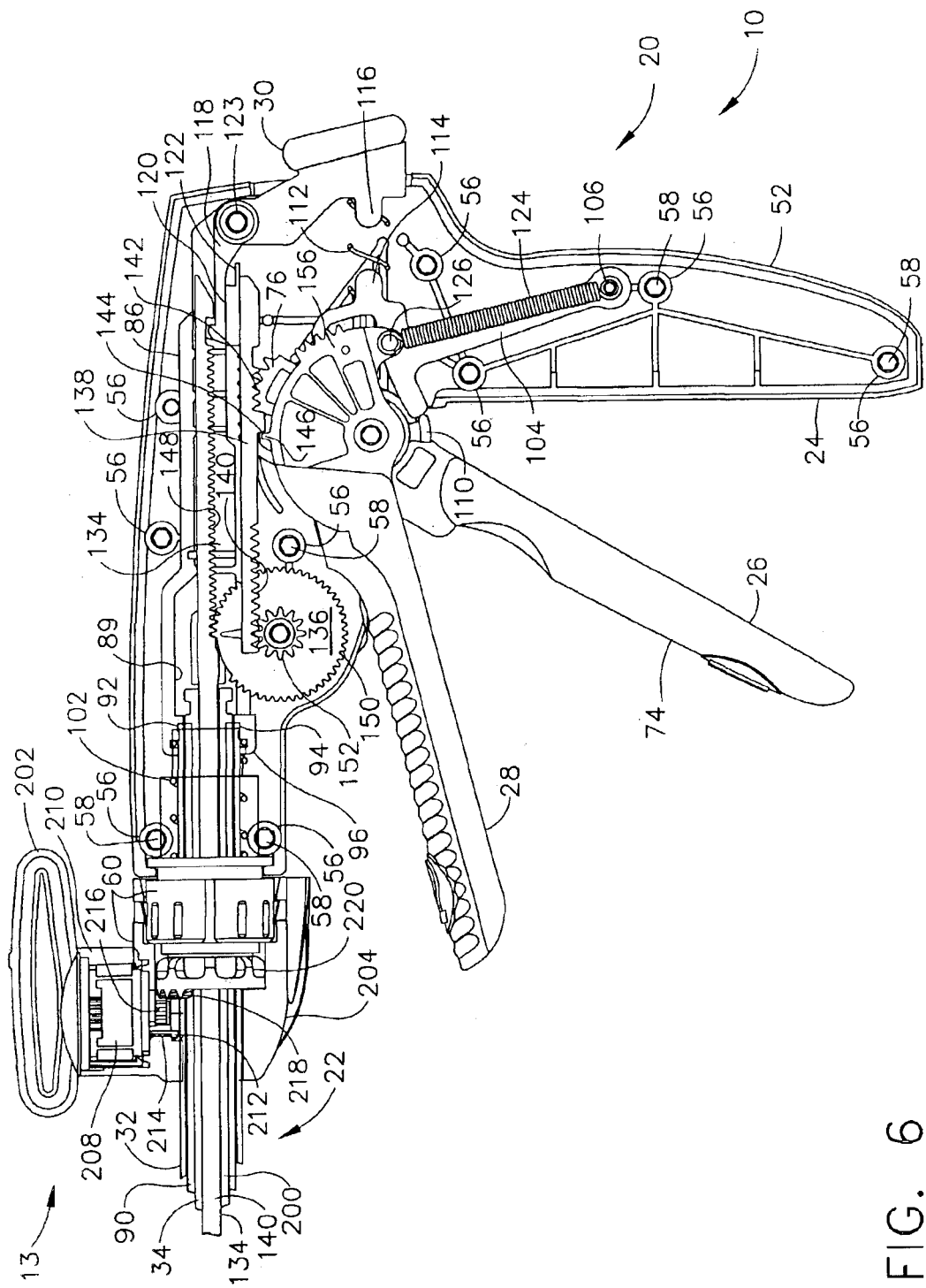
FIG. 6 depicts a side elevation view in section of a handle portion of a proximal end of the surgical instrument of FIG. 1 including a rotating articulation control.
Figure 7:
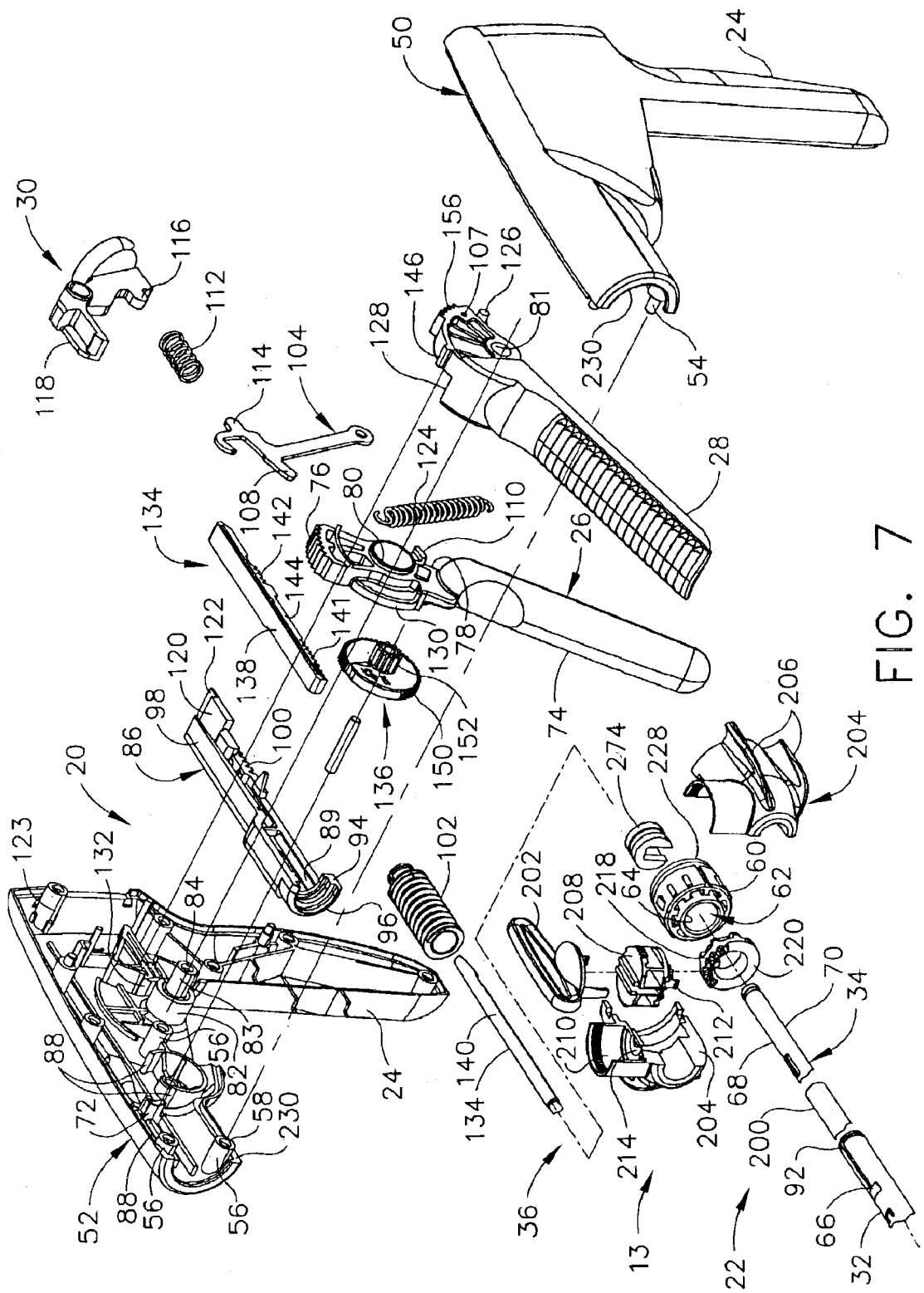
FIG. 7 depicts a perspective, exploded view of the handle portion of the proximal end of the surgical instrument of FIG. 1.
Figure 8:
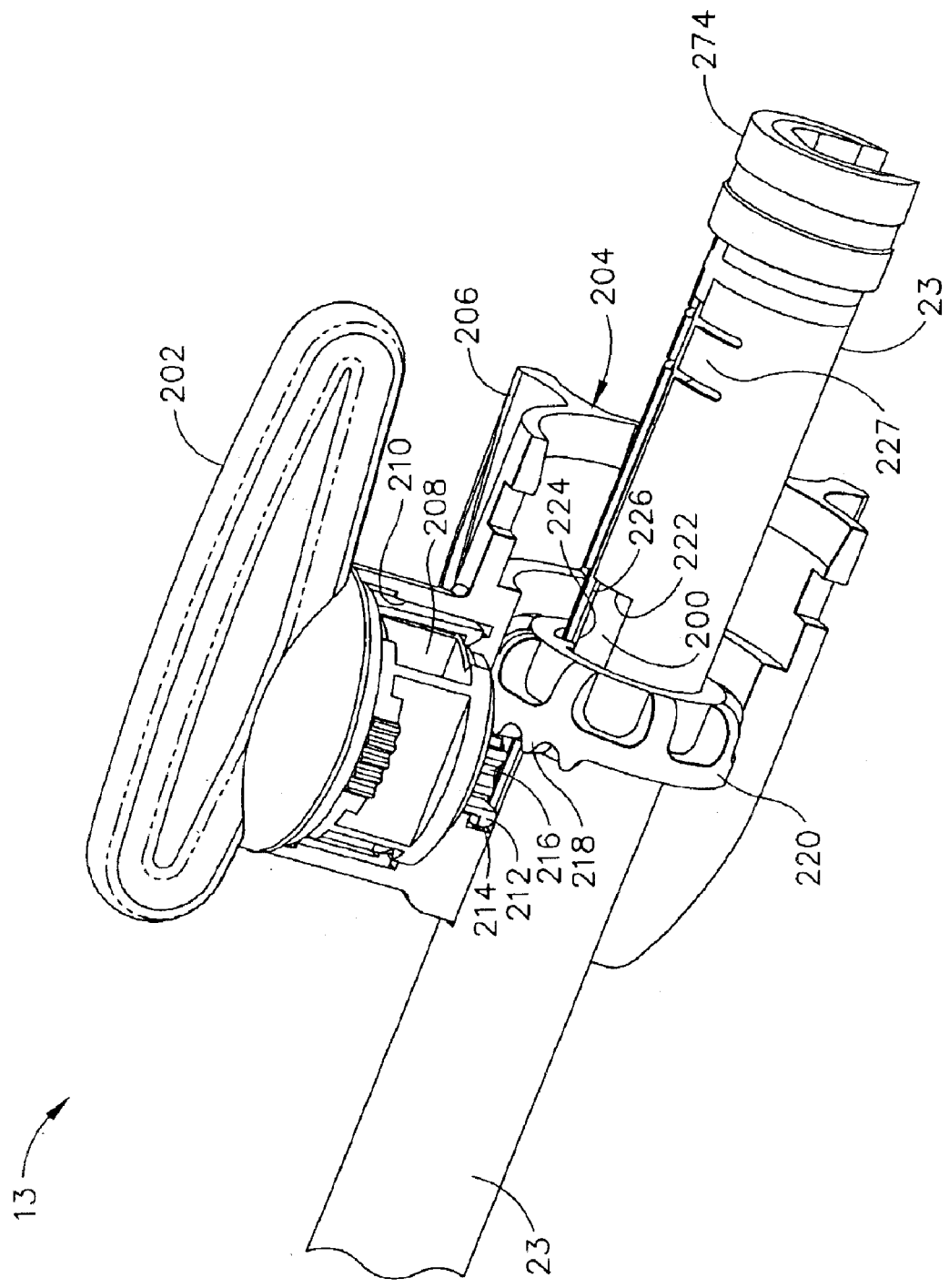
FIG. 8 depicts a perspective view looking downward, forward and to the right of a distal portion of the handle portion of the surgical instrument of FIG. 1 partially cutaway to expose a rotating articulation control mechanism.
Figure 9:
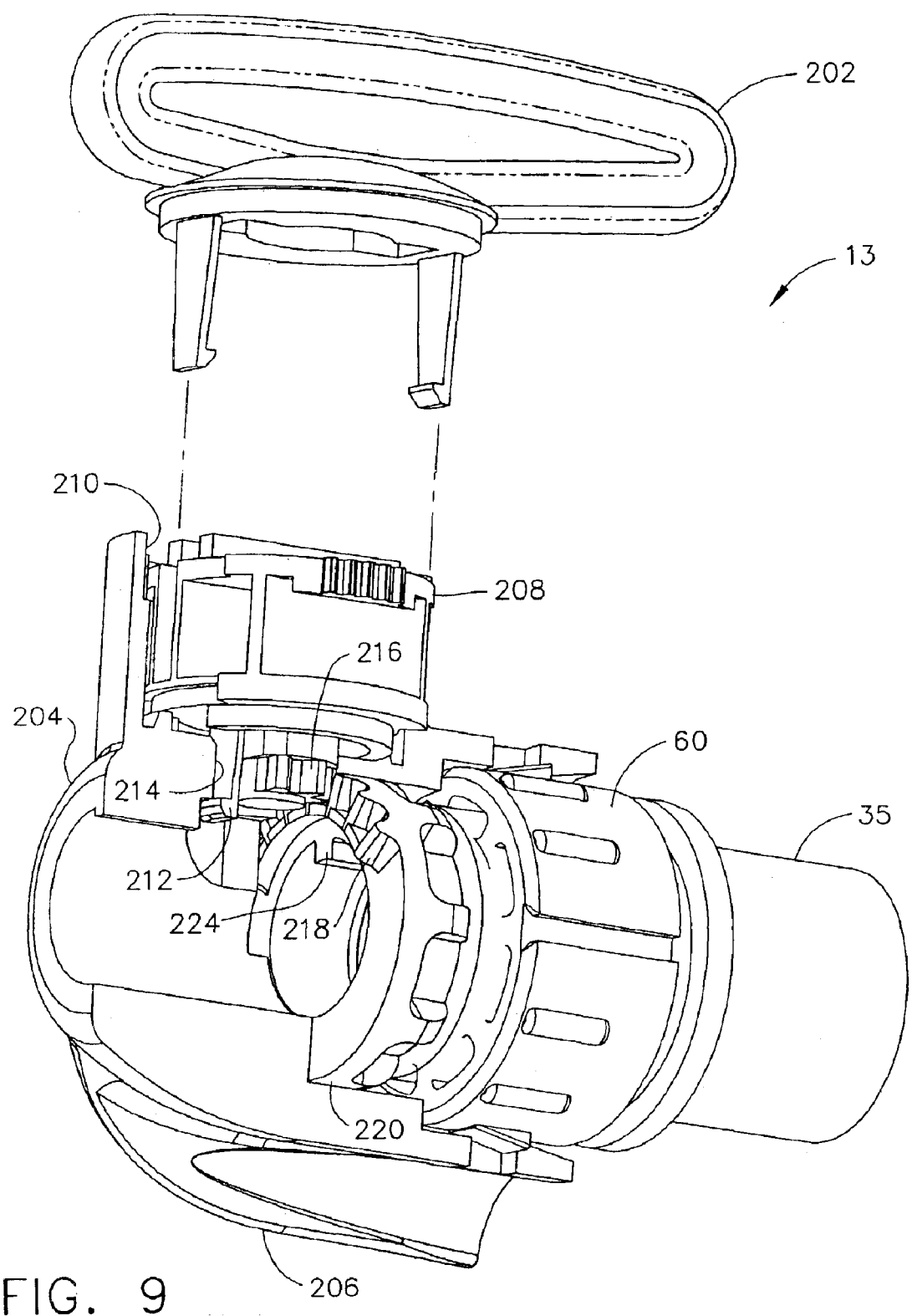
FIG. 9 depicts a perspective view looking upward, rearward and to the right of the distal portion of the handle portion of FIG. 8, partially cutaway to expose the rotating articulation control mechanism and have a rotating articulation control knob disassembled.

With reference to FIGS. 6–7, the handle portion 20 is comprised of first and second base sections 50 and 52, which are molded from a polymeric material such as a glass-filled polycarbonate. The first base section 50 is provided with a plurality of cylindrical-shaped pins 54. The second base section 52 includes a plurality of extending members 56, each having a hexagonal-shaped opening 58. The cylindrical-shaped pins 54 are received within the hexagonal-shaped openings 58 and are frictionally held therein for maintaining the first and second base sections 50 and 52 in assembly.

A housing cap 60 has a bore 62 extending completely through it for engaging and rotating the implement portion 22 about its longitudinal axis. The housing cap 60 includes an inwardly protruding boss 64 extending along at least a portion of the bore 62. The protruding boss 64 is received within a longitudinal slot 66 formed at a proximal portion of the closure sleeve 32 such that rotation of the housing cap 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 3–4) rotates with the housing cap 60.

A proximal end 68 of the frame 34 passes proximally through the housing cap 60 and is provided with a circumferential notch 70 that is engaged by opposing channel securement members 72 extending respectively from the base sections 50 and 52. Only the channel securement member 72 of the second base section 52 is shown. The channel securement members 72 extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotally mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 110 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled, or wedge sled, in the implement portion 22 (not shown in FIG. 6–7) and a metal drive rod 140.

The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter that is smaller than the first diameter.

Rotational Articulation Control

With reference to FIGS. 6–9, the handle portion 20 advantageously incorporates the articulation control 13 that both rotates the implement portion 22 about the longitudinal axis of the surgical instrument 10 and articulates the end effector 12 to an angle with the longitudinal axis. A hollow articulation drive tube 200 is concentrically located within the closure sleeve 32 and is operably coupled to an actuation lever 202 such that rotation of actuation lever 202 rotates tube 200 about the longitudinal axis and causes perpendicular rotation or articulation of the closure ring 250 and end effector 12. This articulation of the closure ring 250 corresponds to the degree and direction of rotation of actuator lever 202 viewed and manipulated by the clinician. In the illustrative version, the relationship is one to one, with the degree of rotation of the actuator lever 202 corresponding to the degree of articulation from the longitudinal axis of the shaft 23, thus providing an intuitive indication to the clinician. It will be appreciated that other angular relationships may be selected.

The articulation control 13 includes a pair of mirrored articulation transmission housings 204 that are attached to the housing cap 60. Moreover, the articulation transmission housing 204 includes longitudinally aligned external tabs 206 that a clinician twists to effect rotation of the articulation transmission housing 204, and thus of the end effector 12, about the longitudinal axis of the implement portion 22. The actuator lever 202 is attached to a cylindrical articulation body 208 that resides within a cylindrical recess 210 opening generally upward and perpendicular to the shaft 23. The lowermost portion of the articulation body 208 includes prongs 212 that snap fit into an opening 214 in the articulation transmission housing 208 near to the shaft 23, the prongs 212 preventing the articulation body 208 from being withdrawn from the cylindrical recess 210.

Annularly presented gear teeth 216 are located about the lower portion of the articulation body 208 and mesh with teeth 218 on an articulation yoke 220. The articulation yoke 220 straddles an articulation rectangular window 222 formed in the closure sleeve 32. Closure sleeve 32 is slidably moveable within the articulation control 13 (in the longitudinal direction) to close and open the end effector 12. The articulation drive tube 200 moves longitudinally with the closure sleeve 32 relative to the fixed articulation control 13. Window 222 provides clearance for a boss 224 inwardly presented from the articulation yoke 220 that passes through the rectangular window 222 to engage a slot 226 in the articulation drive tube 200, longitudinally positioning the articulation drive tube 200 for rotational motion. The hollow articulation drive tube 200 extends longitudinally within the closure sleeve 32 from the articulation mechanism 11 and terminates distally before the locking tabs 227 of the closure sleeve 32. The tabs 227 are inwardly bent behind the proximal face of the articulation drive tube 200 and thereby retaining the articulation drive tube 200 in the shaft 23.

It should be appreciated that the articulation transmission housing 204 is operatively associated to the closure tube 35 of the shaft 23. The housing cap 60 retains the articulation yoke 220 in the articulation transmission housing 204 and retains the articulation control 13 within the handle portion 20 by presenting proximally an outer diameter circular groove 228 that engages a circular inward lip 230 at the distal opening of the assembled base sections 50, 52.

Figure 10:
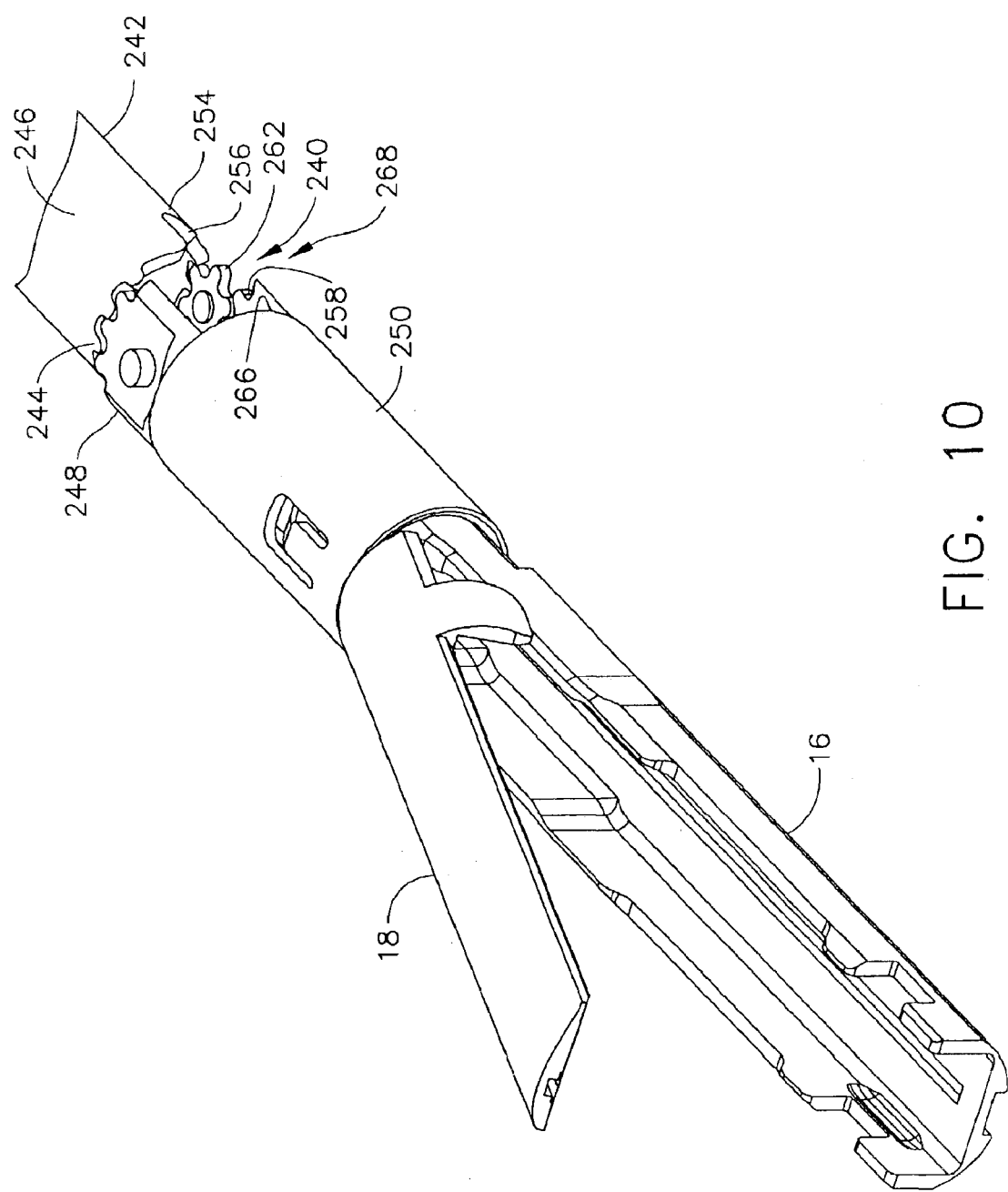
FIG. 10 depicts a top perspective detail view of a spur gear articulation mechanism and end effector of the surgical instrument of FIG. 1 with firing and frame portions removed.
Figure 11:
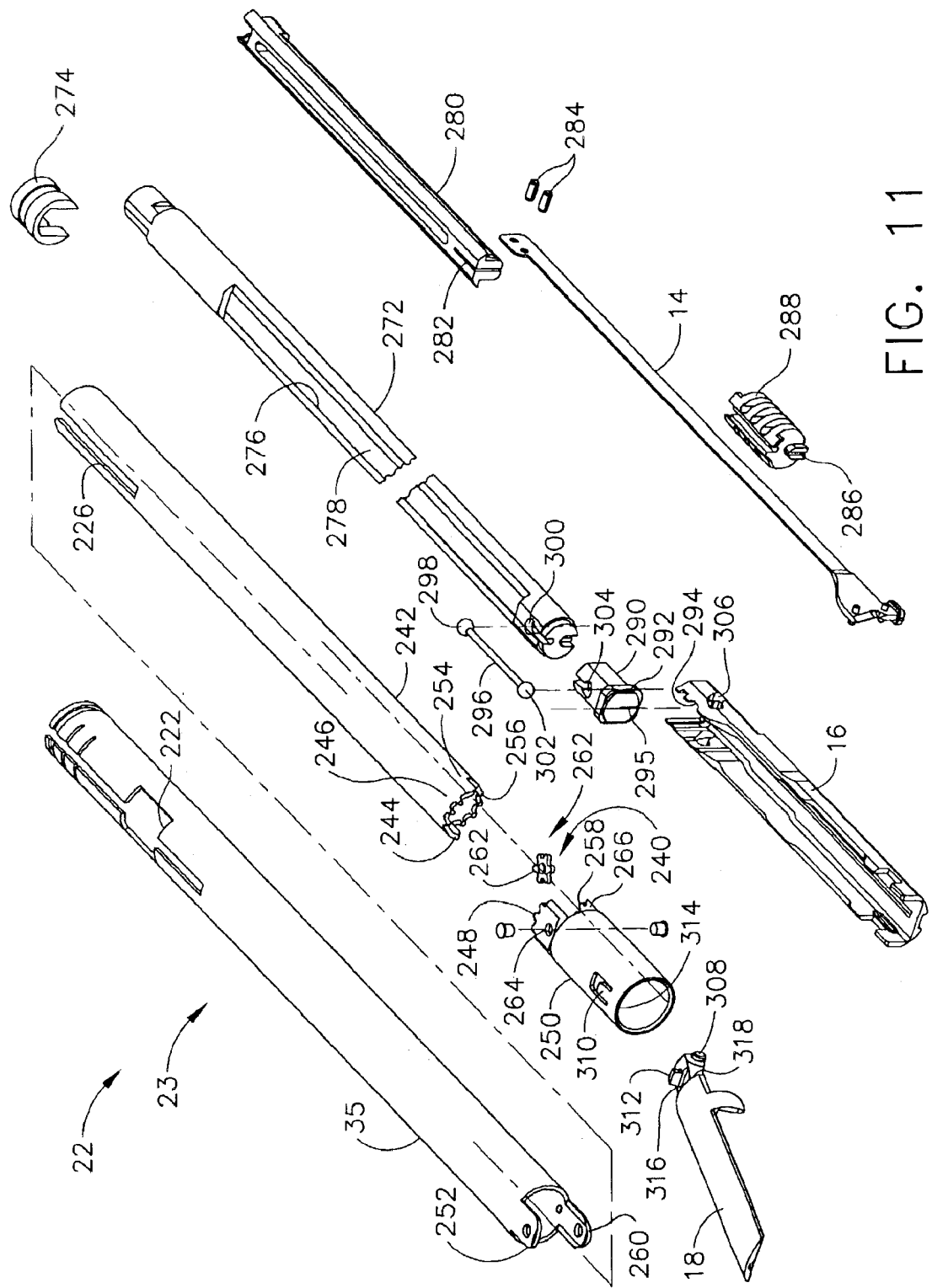
FIG. 11 depicts a perspective, exploded view of an implement portion of the surgical instrument of FIG. 1 including a spur gear articulation mechanism.

FIGS. 10 and 11 depict the gear articulation mechanism 11 of FIGS. 1–2 in the form of a spur gear articulation mechanism 240, which is generally the same as described above but with additional articulation driving components on the other side of the articulation mechanism 240 to thereby increase performance. Articulation mechanism 240 has a rotatable hollow articulation drive tube 242 that is concentrically located within closure sleeve 32 and has a distally projecting gear section 244 about a first circumference portion 246. Gear section 244 meshes with a spur gear 248 attached to and proximally projecting from closure ring 250 which pivots about pins 253 extending through first and second pivot points 252, 260 projecting distally from the closure sleeve 32. Thus, an articulation pivot axis passes through both the first and second pivot points 252, 260 and pins 253 rotatably couple closure ring 250 to the closure sleeve 32. Rotation of drive 242 engages the gears 242 and 248 and articulates closure ring 250 about first and second pivot points 252, 260.

To increase the effective surface area of gear contact between the hollow articulation drive tube 242 and the closure ring 250, a second circumference portion 254 of the hollow articulation drive tube 242 has a recessed distally projecting gear section 256 extending therefrom. Gear section 256 is operably coupled to a second spur gear 258 attached to and proximally projecting from an opposite lateral side of the closure ring 250 by a reversing gear 262 pivotally supported by the frame 34. Reversing gear 262 engages both the recessed distally projecting gear section 256 on one side and the second spur gear 258 of the closure ring 250 on the other.

When the closure trigger 26 is actuated, both the hollow articulation drive tube 242 and pivotally attached closure tube 250 of the closure sleeve 32 are moved distally to close the anvil 18. The closure tube 35 of the closure sleeve 32 is spaced away from the closure ring 33 by pivot points 252, 260 pinned to pivot holes 264 and 266 centered in spur gears 248, 258, and a frame opening 268 that extends therethrough. The frame opening 268 provides clearance so that the proximal edges of the closure ring 33 and the distal edges of the closure tube 35 of the closure sleeve 32 do not collide during articulation.

FIG. 11 depicts in disassembled form an implement portion 270 that includes the spur gear articulation mechanism 240. A frame 272 is longitudinally attachable to the handle portion 20 (depicted in FIGS. 1 and 2) with a bushing 274 on its proximal end for rotatingly engagement thereto. A frame trough 276 formed by an opening 278 longitudinally aligned with the center of the frame 272 is longer than a firing connector 280 that slides longitudinally within the frame trough 276. The proximal end of the firing connector 280 rotatingly engages the distal end of the metal drive bar 140 (depicted in FIG. 6). The distal end of the firing connector 280 includes a slot 282 that receives a proximal end of the firing bar 14, attached therein by pins 284. A more distal portion of the firing bar 14 is positioned within a lower groove 286 in a firing bar slotted guide 288 that is distally engaged with an articulating frame member 290 and the frame 272.

Articulating frame member 290 has a channel-anchoring member 292 that distally attaches to an attachment collar 294 of a proximal portion in the elongate channel 16. The firing bar 14 passes through a lower slot 295 in the articulating frame member 290. The articulating frame member 290 is spaced away from the distal end of the frame 272 by the firing bar slotted guide 288 and flexibly attached thereto for articulation by a resilient connector 296. A widened proximal end 298 of the resilient connector 296 engages a distally communicating top recess 300 in the distal end of the frame 272 and a widened distal end 302 of the resilient connector 296 engages a proximally communicating top recess 304 in the articulating frame member 290. Thereby, the elongate channel 16 is attached to the handle portion 20, albeit with a flexible portion therebetween.

The elongate channel 16 also has an anvil cam slot 306 that pivotally receives an anvil pivot 308 of the anvil 18. The closure ring 250 that encompasses the articulating frame member 290 includes a distally presented tab 310 that engages an anvil feature 312 proximate but distal to the anvil pivot 308 on the anvil 18 to thereby effect opening. When the closure ring 250 is moved forward, its distally presented closing face 314 contacts a ramped cylindrical closing face 316, which is distal to tab 312 of the anvil 18. This camming action closes the anvil 18 downward until the closing face 314 of the closure ring 250 contacts a flat cylindrical face 318 of the anvil 18.

Support Plates

Figure 12:
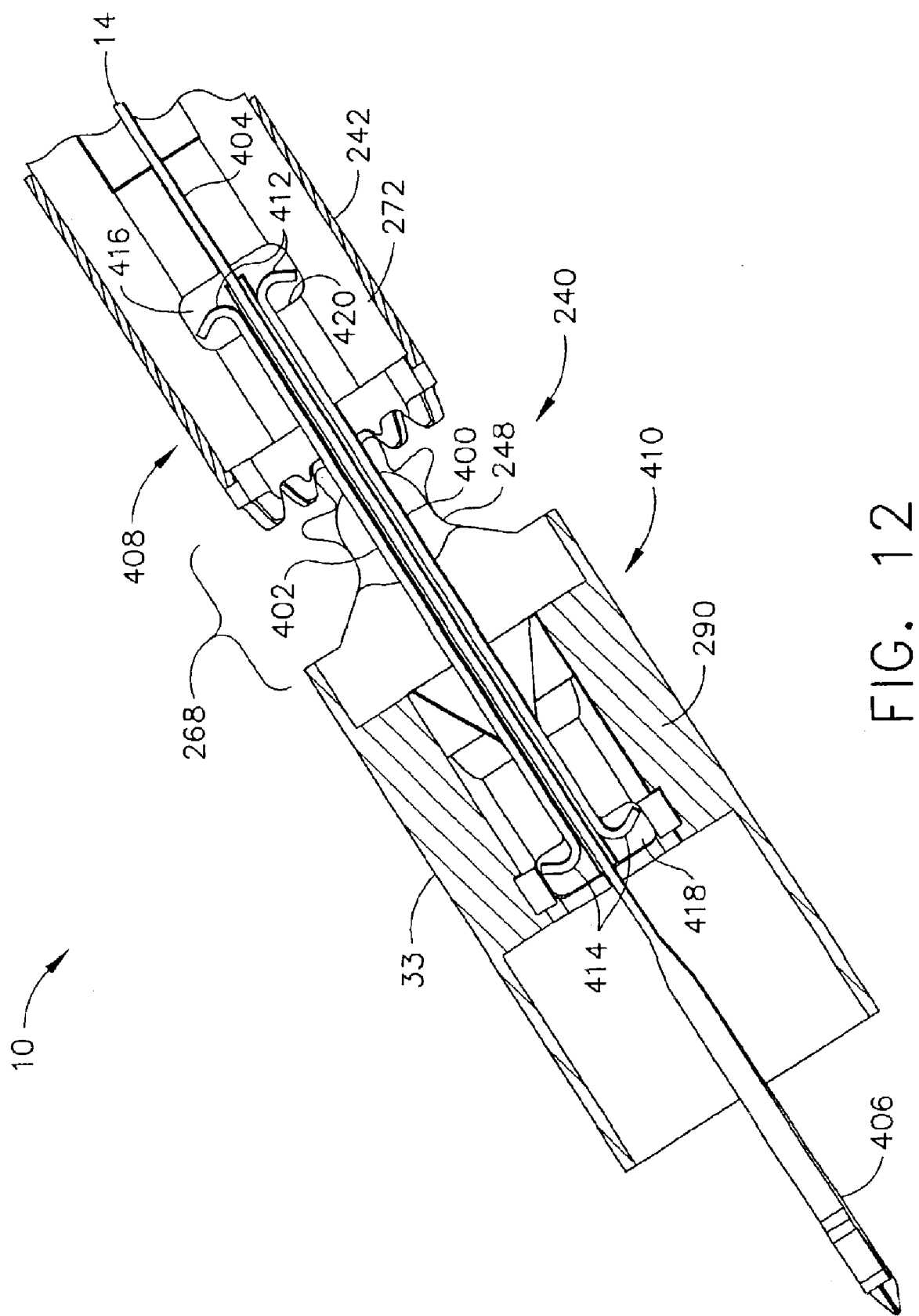
FIG. 12 depicts a top sectional view of the spur gear articulation mechanism of FIG. 11.
Figure 13:
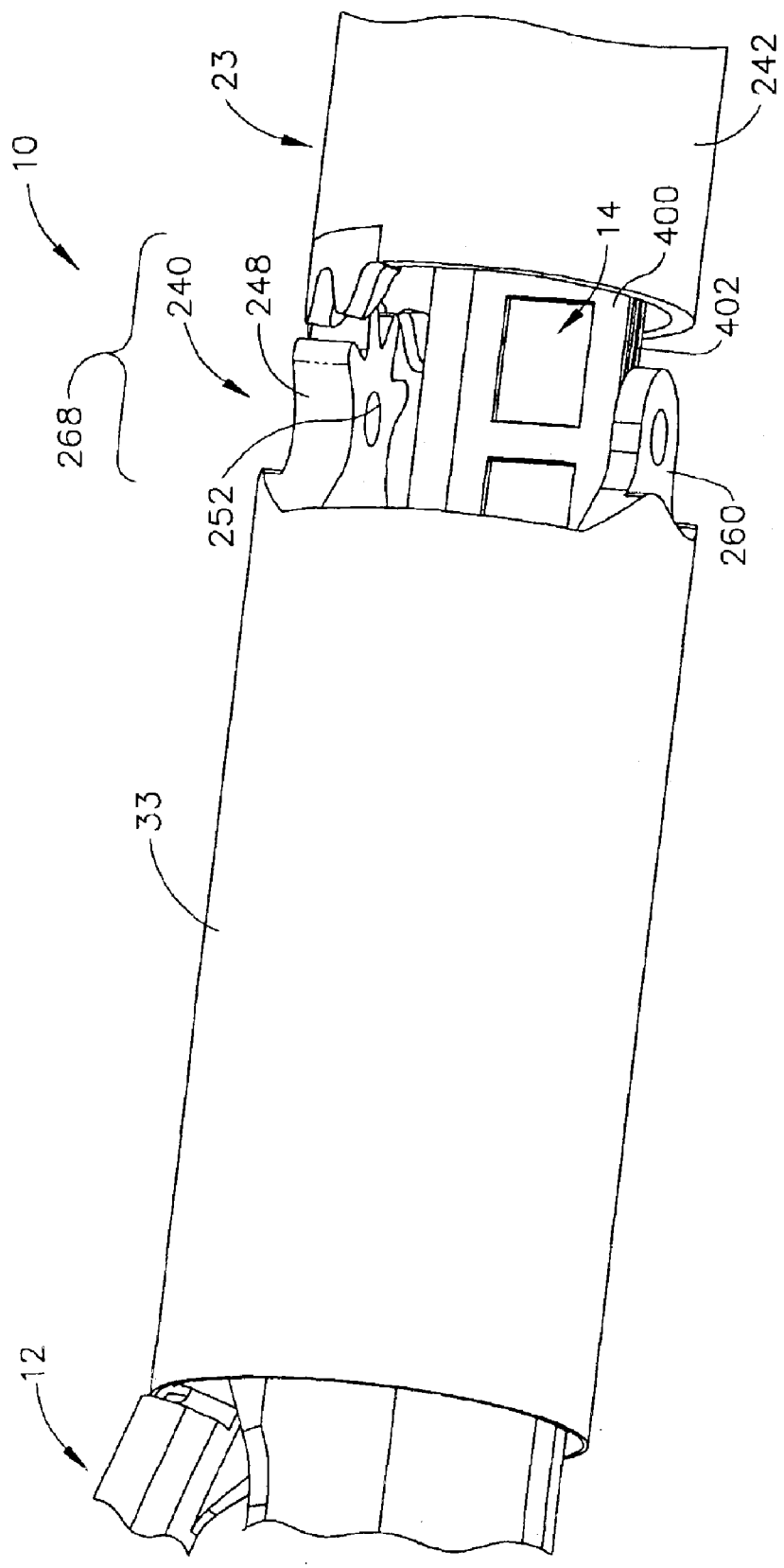
FIG. 13 depicts a perspective detail view of the spur gear articulation mechanism of FIG. 11.

FIGS. 12–13 depict the articulation mechanism 240 along the articulation pivot axis illustrating flexible support structures between the shaft 23 and the end effector 12 and a construction of the firing bar 14 that advantageously performs severing yet is flexible enough for articulation. The hollow articulation drive tube 242 engages the spur gear 248 of the closure ring 33. Omitted from this view are the proximal portion 35 of the closure sleeve 32 (i.e., closure tube 35) that longitudinally positions for articulation the spur gear 248 at an upper pivot point 252 and the lower pivot point 260.

Resilient support in the articulation mechanism 240 allow articulation about the articulation pivot axis includes a pair of support plates 400, 402 that flank a proximal portion of the firing bar 14 to prevent buckling as they pass through the frame opening 268. Thus, the firing bar 14 is capable of transferring large loads while being flexible. This proximal portion of the firing bar 14 is depicted as an elongate tapered firing strip 404 formed as one or more flat blades of spring material that are aligned for flexing about the articulation pivot axis. This tapered firing strip 404 transitioned to a thicker distal portion, depicted as a firing bar head 406, that includes the cutting edge 48, upper pin 38, middle pin 46 and firing bar cap 44 (pins omitted in FIG. 12). This thicker firing bar head 406 has increased thickness to resist deflection during firing, thereby ensuring an effective severing and actuation of the staple cartridge 37. The thinner cross section of the tapered firing strip 404 is more susceptible to buckling when subjected to peak firing loads. The support plates 400, 402 advantageously mitigate the effects of peak firing loads in the tapered firing strip 404 by supporting the tapered firing strip 404 through the articulation joint to prevent buckling of the firing bar 14. Support plates 400, 420 are longitudinally moveable within both of the proximal and distal sides 408, 410 of the articulation mechanism 240.

As shown in FIG. 12, the pair of support plates 400, 402 each have a proximal and distal sliding spring ends 412, 414, received respectively by a frame pocket 416 in the frame 32 and an end frame pocket 418 in the articulating frame member 290. These pockets 416, 418 provide clearance for the spring ends 412, 414 of the support plates 400, 402 to move within as the articulation mechanism 240 articulates, lessening the frame opening 268 toward the inside and lengthening the frame opening 268 toward the outside. Reversing the direction of articulation of the end effector 12 reverses movement of the spring ends 412, 414 (not shown). Insofar as the proximal spring ends 412 tend not to be rigidly engaged to a distal extreme surface 420 of the frame pocket 416, the support plates 400, 402 are able to springedly move distally in response to a peak firing load in the firing bar 14.

Figure 14:
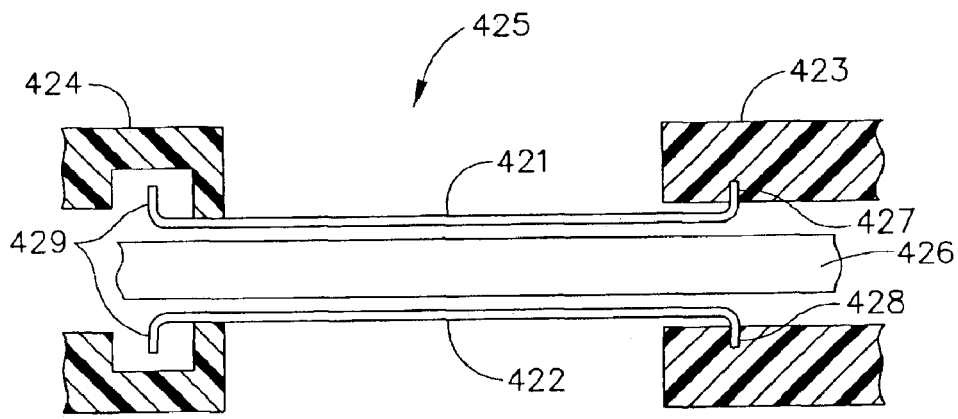
FIG. 14 depicts a top view in section of a prior art articulation support plate assembly.
Figure 15:
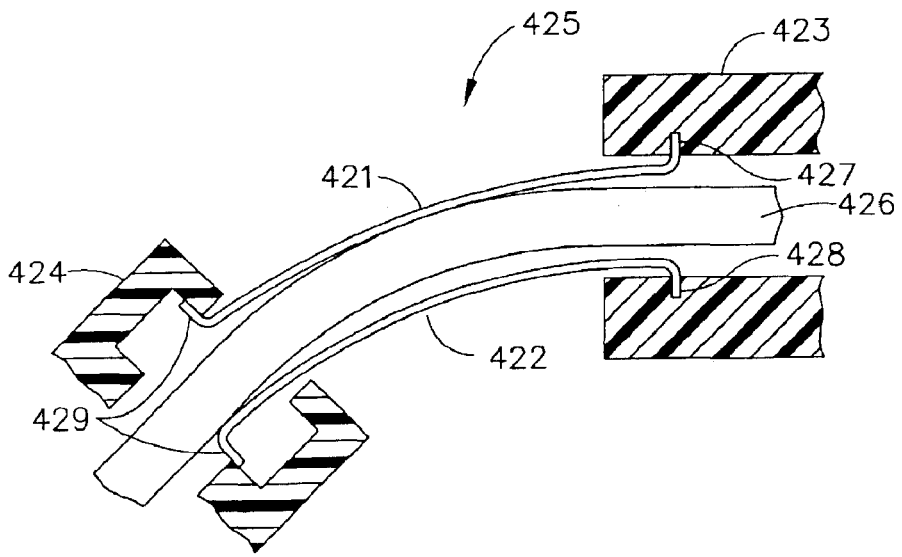
FIG. 15 depicts a top view in section of the prior art articulation support plate assembly of FIG. 14 in an articulated position.

By contrast, FIGS. 14–15 depict known Prior Art support members 421, 422 formed from a spring material that rigidly attach to a proximal side 423 and slidingly contact a distal side 424 of a known articulation mechanism 425. In FIG. 14, the instrument is shown straight or un-articulated and a pair of free or distal ends 429 of the support plates 421, 422 are centered within end frame pockets 418 and fixed ends 427, 428 are fixedly attached to proximal side 423. With particular reference to FIG. 15, the end effector is shown articulated and a firing bar 426 and support plates 421, 422 are bent from the articulation. Since the support plates 421, 422 are spring cantilever beams, they contact the firing bar 426 as shown and the free or distal ends 429 of the support plates 421, 422 move proximally and distally, respectively, within end frame pockets 418. The contact of the free or distal ends 429 of support plates 421, 422 with the firing bar can induce drag loads and increase the force needed to move the firing bar 426.

Figure 16:
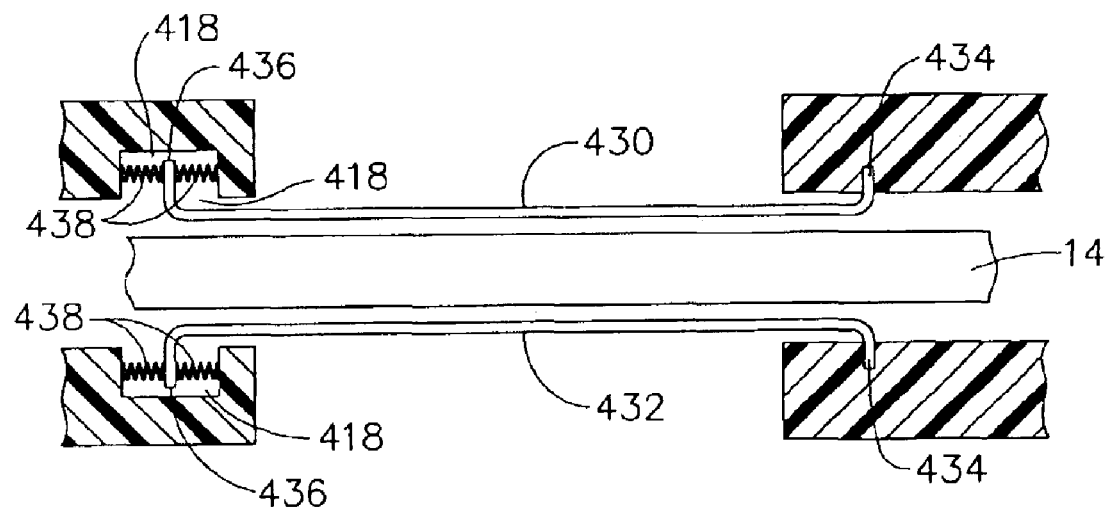
FIG. 16 depicts a top view in section of a springedly-coupled, single free-end support plate assembly for the surgical instrument of FIG. 1.

FIG. 16 depicts support plates 430, 432 that alternatively each include a rigidly attached proximal ends 434 and a springedly attached distal ends 436 in the end frame pocket 418 by opposing compression springs 438 engaging each end 436. Springedly attaching the distal ends 436 to the frame pockets 418 provides additional control of the free distal ends to reduce drag on the firing bar 14 and enables the ends 436 to move longitudinally during articulation. Alternatively, the spring attachment provided by the compression springs 438 may be reversed, engaging the proximal ends 434 with the distal ends 436 rigidly attached.

Figure 17:
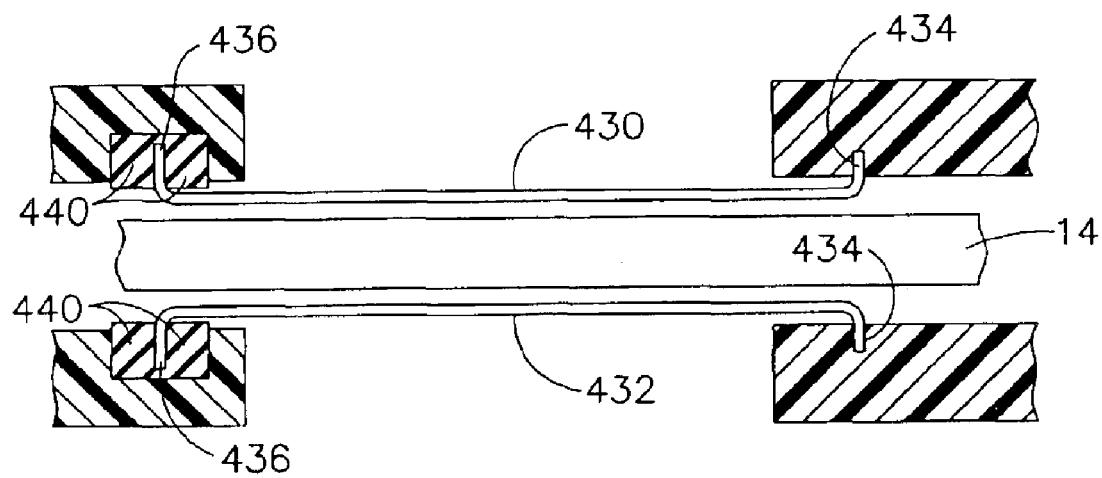
FIG. 17 depicts a top view in section of a resilient-coupled, single free-end support plate assembly for the surgical instrument of FIG. 1.

FIG. 17 depict the support plates 430, 432 of FIG. 16 with a resilient member 440 engaging each the distal ends 436 of each support plate 430, 432. Alternatively, the resilient attachment by the resilient members 440 may be reversed, engaging the proximal ends 434 with the distal ends 436 rigidly attached. Resilient members may be formed from various elastomeric materials such as silicone, rubber, buna-n or any one of a number of known elastomers that behave elastically. Foam materials can also act as a spring and can include closed or open cell foams formed from a wide variety of materials such as silicone foams, rubber based foams or polyethylene foams.

Figure 18:
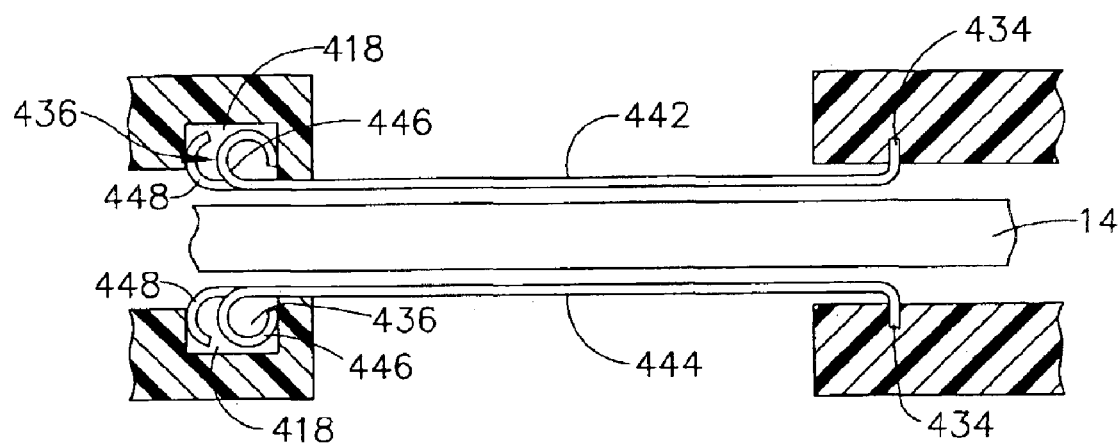
FIG. 18 depicts a top view in section of a spring-fingered, single free-end support plate assembly for the surgical instrument of FIG. 1.
Figure 19:
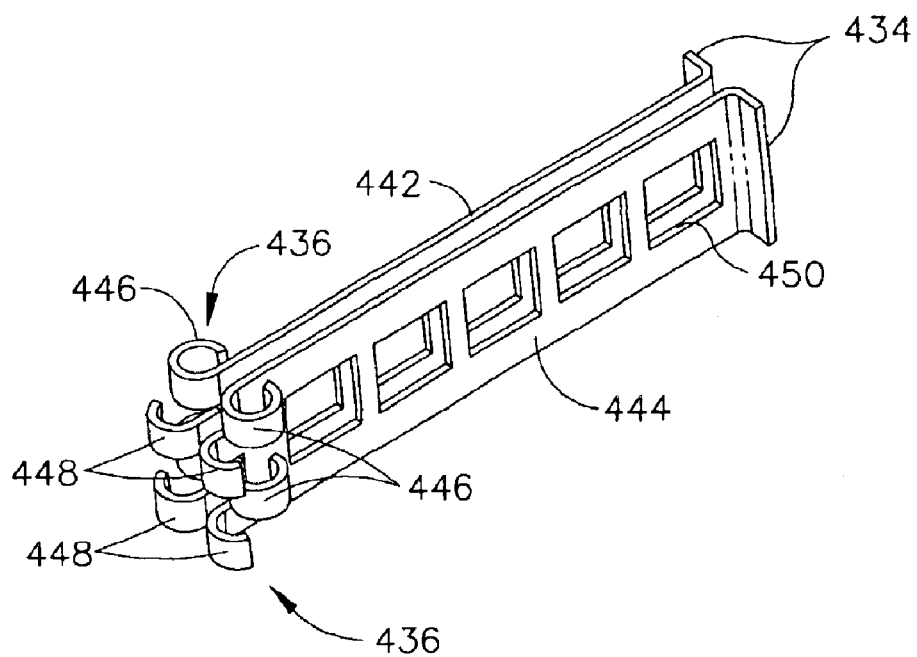
FIG. 19 depicts a perspective view of the spring-fingered, single free-end support plates of FIG. 18.

FIGS. 18–19 depict support plates 442, 444 that include inner and outer bent spring fingers 446, 448 that springedly engage the end frame pocket 418 so that the spring plates 442, 444 absorb peak firing loads from the firing bar 14. Alternatively, the spring engagement may be reversed, with the proximal ends 434 including inner and outer bent spring fingers 446, 448 engaging a proximal frame pocket 416 (not depicted in FIGS. 18–19) with the distal ends 436 rigidly attached. FIG. 19 depicts how additional flexibility may be obtained along the span of the support plate 442, 442 by introducing openings 450 therein.

Figure 20:
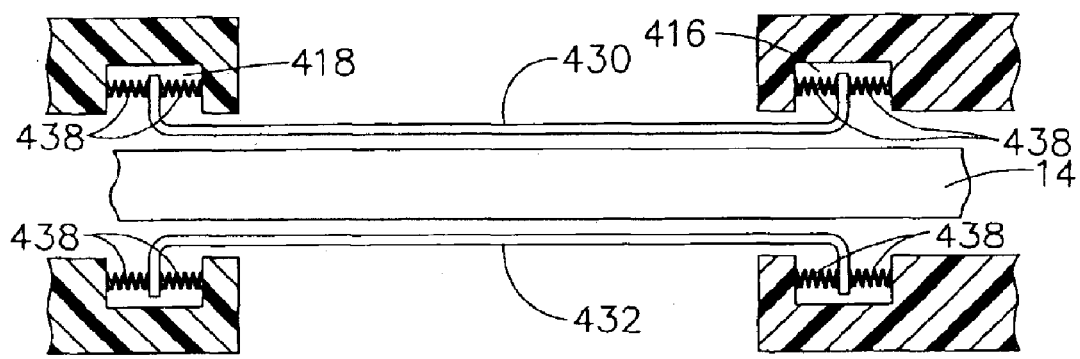
FIG. 20 depicts a top view in section of a springedly-coupled, dual free-end support plate assembly for the surgical instrument of FIG. 1.

FIG. 20 depicts the support plates 430, 432 of FIG. 16 with both a frame pocket 416 and an end frame pocket 418 incorporating opposing compression springs 438 to further mitigate the effects of firing bar loads.

Figure 21:
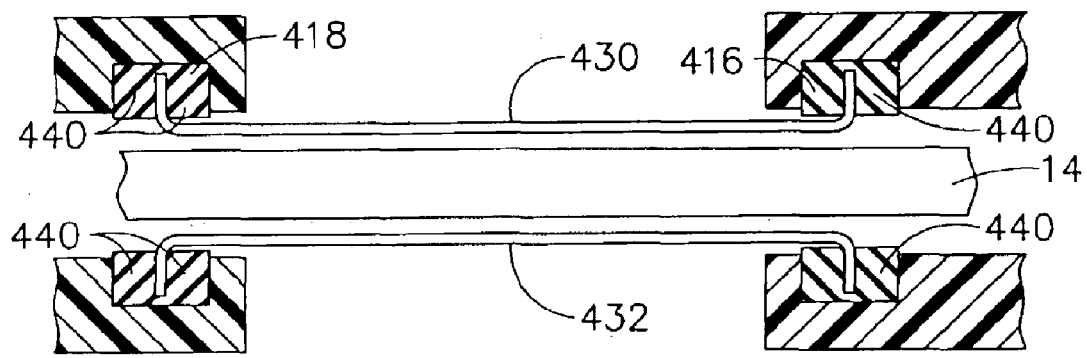
FIG. 21 depicts a top view in section of a resilient-coupled, dual free-end support plate assembly for the surgical instrument of FIG. 1.

FIG. 21 depicts the support plates 430, 432 of FIG. 17 with both a frame pocket 416 and an end frame pocket 418 incorporating resilient members 440 to further mitigate the effects of firing loads on the firing bar 14.

Figure 22:
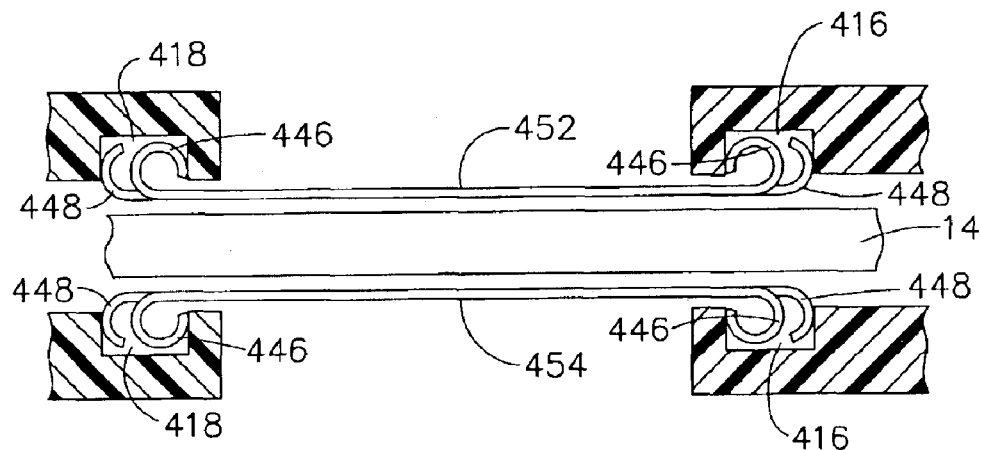
FIG. 22 depicts a top view in section of a spring-fingered, dual free-end support plate assembly for the surgical instrument of FIG. 1.

FIG. 22 depicts support plates 452, 454 that include inner and outer bent spring fingers 446, 448 on both ends that springedly engage both a frame pocket 416 and an end frame pocket 418 to further mitigate the effects of firing bar loads.

Figure 23:
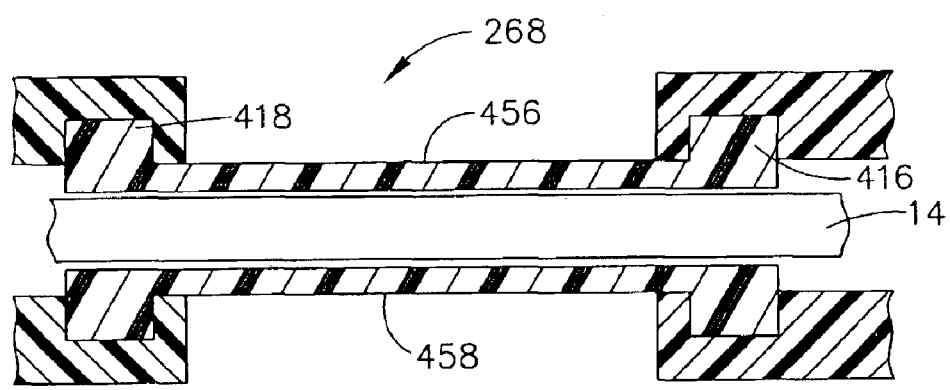
FIG. 23 depicts a top view in section of a resilient support plate assembly for the surgical instrument of FIG. 1.

FIG. 23 depicts resilient support plates 456, 458 that each engage frame pocket 416 and end frame pocket 418 to adjust to the changes in spacing on the inside and outside of the frame opening 268 by expanding or compressing in response thereto. Resilient support plates can be made from a number of materials with flexible or elastomeric properties including; silicone, rubber, buna-n Isoplast or any one of a number of known elastomers that behave elastically or resiliently.

Figure 24:
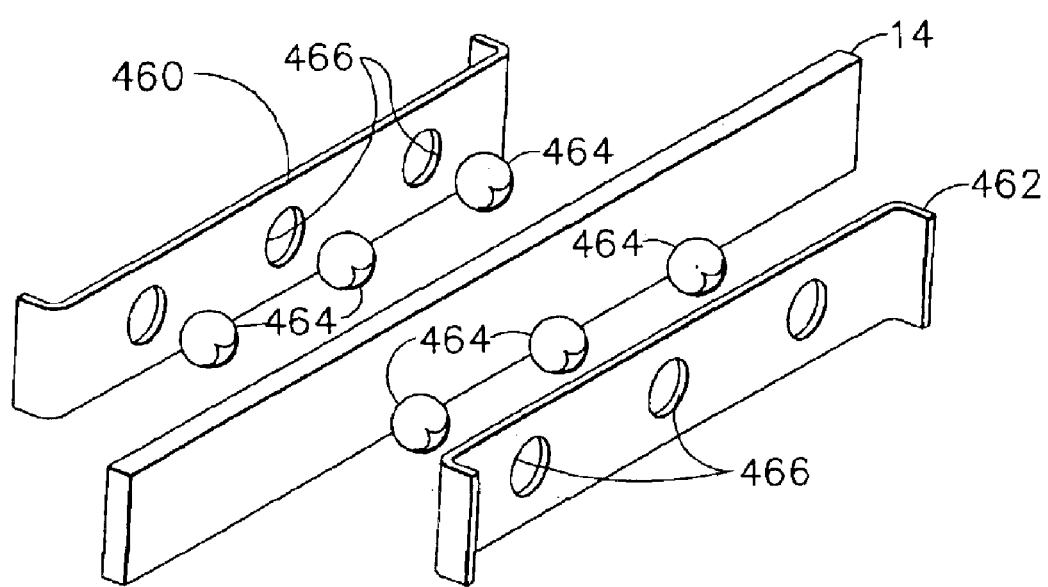
FIG. 24 depicts a perspective, exploded view of a pair of support plates with bearing contact to a firing bar for the surgical instrument of FIG. 1.

FIG. 24 is an exploded view of low friction support plates 460, 462 that incorporate bearings 464 to reduce frictional forces between the firing bar 14 and the support plates 460, 462. The support plates 460, 462 have dimpled openings 466 respectively for the reception of bearings 464 to hold them into contact with the firing bar 14. Alternatively, cylindrical bearings may be incorporated with the cylindrical bearings oriented for distal movement of the firing bar 14.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

The present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

For another example, although the E-beam firing beam 14 has advantages for an endoscopically employed surgical severing and stapling instrument 10, a similar E-Beam may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

For yet another example, although an illustrative handle portion 20 described herein is manually operated by a clinician, it is consistent with aspects of the invention for some or all of the functions of a handle portion to be powered (e.g., pneumatic, hydraulic, electromechanical, ultrasonic, etc.). Furthermore, controls of each of these functions may be manually presented on a handle portion or be remotely controlled (e.g., wireless remote, automated remote console, etc.).

As yet an additional example, although a simultaneous stapling and severing instrument is advantageously illustrated herein, it would be consistent with aspects of the invention supporting a firing mechanism through an articulating shaft with other types of end effectors, such as cutters, staplers, clip applier, access device, drug/gene therapy delivery device, and a energy device using ultrasound, RF, laser, etc.

For example, various combinations of rigidly attached, resiliently attached, and springedly attached support plate ends may be used, such as resilient attached proximal end and a springedly attached distal end.

What is claimed is:

1. A surgical instrument, comprising:
   a handle portion operably configured to produce an articulation motion and a firing motion;
   a shaft having a longitudinal axis attached to the handle portion for transferring the articulation motion and the firing motion;
   an articulation mechanism coupling the shaft to the end effector and responsive to the articulation motion to rotate the end effector from the longitudinal axis of the shaft;
   an end effector distally attached to the articulation mechanism;
   a firing mechanism responsive to the firing motion and coupled for movement through the articulation mechanism and end effector in response to the firing motion;
   a pair of support plates flanking the firing mechanism across the articulation mechanism,
   each support plate including ends having a pair of springs longitudinally coupled with both sides of a frame recess formed in the articulation mechanism.

2. The surgical instrument of claim 1, wherein the handle portion comprises a handle means for producing a rotational articulation motion and a longitudinal firing motion, and the shaft comprises a shaft means for separately transferring the rotational articulation motion and the longitudinal firing motion.

3. The surgical instrument of claim 2, wherein the handle means further comprises a means for producing a longitudinal closing motion, and the shaft means further comprises a means for separately transferring the longitudinal closing motion.

4. A surgical instrument comprising:
   a handle portion operable to produce a firing motion, a closing motion, and an articulation motion;
   a shaft coupled to the handle portion operable to separately transfer the firing motion, the closing motion, and the articulation motion;
   an elongate channel coupled to the shaft;
   an anvil pivotally coupled to the elongate channel, responsive to the closing motion from the shaft;
   a firing device including a distally presented cutting edge longitudinally received between the elongate channel and the anvil;
   an articulation mechanism pivoting the elongate channel from the shaft in response to the articulation motion;
   a pair of support plates flanking the firing mechanism across the articulation mechanism,
   each support plate including ends having a pair of springs longitudinally coupled with both sides of a frame recess formed in the articulation mechanism.

5. The surgical instrument of claim 4, wherein the firing device engages the anvil and elongate channel to affirmatively space the anvil from the elongate channel during longitudinal travel between the anvil and elongate channel.

6. The surgical instrument of claim 4, wherein the firing device further comprises a distally presented cutting edge, the surgical instrument further comprising a staple cartridge engaged by the elongate channel and including a proximally opened slot for receiving the cutting edge of the firing device, the staple cartridge including a plurality of staples cammed upwardly by the distal longitudinal movement of the firing device.

7. A surgical instrument, comprising:
   a handle portion operably configured to produce a rotational articulation motion and a longitudinal firing motion;
   a shaft operably configured to separately transfer the rotational articulation motion and the longitudinal firing motion;
   an end effector distally coupled to the shaft means;
   an articulation mechanism responsive to the rotational articulation motion to articulate the end effector;
   a firing bar responsive to the longitudinal firing motion of the handle portion, the firing bar comprising:
      an elongate strip longitudinally positioned for movement through the articulation mechanism, and
      a firing bar head distally connected to the elongate strip and positioned for longitudinal movement in the end effector;
   a support plate means for providing articulating support flanking the firing bar elongate strip through the articulation means; and
   each support plate means including ends having a pair of springs longitudinally coupled with both sides of a frame recess formed in the articulation means.

* * * * *